(12) United States Patent
Snijders

(10) Patent No.: US 8,733,211 B2
(45) Date of Patent: May 27, 2014

(54) TATTOO MACHINES, METHODS OF MAKING TATTOO MACHINES, AND METHODS OF USING TATTOO MACHINES

(76) Inventor: Michael Snijders, Fontana, CA (US)

( * ) Notice: Subject to any disclaimer, the term of this patent is extended or adjusted under 35 U.S.C. 154(b) by 290 days.

(21) Appl. No.: 13/366,935

(22) Filed: Feb. 6, 2012

(65) Prior Publication Data
US 2012/0209307 A1    Aug. 16, 2012

Related U.S. Application Data

(60) Provisional application No. 61/443,367, filed on Feb. 16, 2011.

(51) Int. Cl.
*A61M 37/00*    (2006.01)
*A61B 17/34*    (2006.01)
*A01K 11/00*    (2006.01)

(52) U.S. Cl.
CPC ............ *A61M 37/00* (2013.01); *A61M 37/0076* (2013.01); *A01K 11/005* (2013.01)
USPC ................................ 81/9.22; 606/186; 30/362

(58) Field of Classification Search
USPC ...................... 81/9.22; 30/358, 362, 366, 367; 606/185, 186
See application file for complete search history.

(56) References Cited

U.S. PATENT DOCUMENTS

| | | | | |
|---|---|---|---|---|
| 3,509,786 | A | * | 5/1970 | Buttner ........................... 81/9.22 |
| 4,204,438 | A | * | 5/1980 | Binaris et al. ................... 81/9.22 |
| 4,864,276 | A | | 9/1989 | Tribbey et al. |
| 4,914,988 | A | * | 4/1990 | Chang ............................ 81/9.22 |
| 5,107,155 | A | | 4/1992 | Yamaguchi |
| 5,165,488 | A | * | 11/1992 | Liu ................................. 173/49 |
| 6,033,421 | A | | 3/2000 | Theiss et al. |
| 6,636,007 | B2 | | 10/2003 | Hong et al. |
| 6,765,331 | B2 | | 7/2004 | Koyanagi et al. |

* cited by examiner

*Primary Examiner* — David B Thomas
(74) *Attorney, Agent, or Firm* — Loza & Loza, LLP; Tyler J. Barrett

(57) ABSTRACT

Tattoo machines include a motor pivotably coupled to a frame. The motor includes an eccentrically weighted shaft. A needle drive mechanism is coupled with the motor. Methods of making tattoo machines may include obtaining a frame and obtaining a motor that includes an eccentrically weighted shaft. The motor can then be coupled to the frame so that the motor is able to pivot about a pivot axis. Methods operational for tattoo machines include rotating an eccentrically weighted shaft on a motor that is pivotably coupled to a frame. The motor is pivoted about a pivot axis as a result of the rotation of the shaft.

20 Claims, 4 Drawing Sheets

TATTOO MACHINES, METHODS OF MAKING TATTOO MACHINES, AND METHODS OF USING TATTOO MACHINES

CROSS-REFERENCE TO RELATED APPLICATIONS

The present Application for Patent claims priority under 35 U.S.C. §119 to Provisional Application No. 61/443,367 entitled Tattoo Machines, Methods of Making Tattoo Machines, and Methods of Using Tattoo Machines, which is hereby expressly incorporated by reference in its entirety herein.

TECHNICAL FIELD

Various features of the present disclosure relate to tattoo machines, methods of making tattoo machines and methods of using tattoo machines. More particularly, one or more implementations of the present disclosure relate to tattoo machines employing a motor adapted to drive the linear motion of a tattoo needle.

BACKGROUND

Tattoo machines have been in use for many years. A tattoo machine typically has a reciprocating needle that moves up and down within a tubular structure, carrying ink into the skin of an individual in the process. The reciprocating needle typically punctures the skin at a high rate. The needles are installed in the machine and dipped in ink, which is sucked up through the machine's tube system. Then, the tattoo machine induces an up-and-down motion of the needle to puncture the top layer of the skin and drive insoluble particles of ink into the dermal layer of skin.

Mechanically speaking, conventional tattoo machines typically comprise either a coil tattoo machine or a rotary tattoo machine. Coil tattoo machines are more widely used currently due to their relative availability and relatively lower cost. A coil tattoo machine employs an electromagnetic circuit to move the needle grouping up and down. Differentiations and variants can be found in a wide array, ranging from single coiled machines to triple coiled machines. Generally, the coil tattoo employs one or more DC coils and spring point(s) that induce the linear up and down motion of a bar that is coupled to the needle. Coil tattoo machines typically allow some "give" in the needle (i.e., absorb some of the force resulting when the needle impacts the skin), inhibiting blowout that is caused when the needle extends too far into or beyond the dermal layer of skin. However, coil tattoo machines are generally relatively heavy and more difficult to maneuver during use. In addition, the electromagnetic switching of coil type tattoo machines generates a significant amount of noise, which can turn off first-time customers who may already be hesitant about getting a tattoo. Further, coil tattoo machines can be used as either a liner or a shader, but not both, since shaders generally have thicker barrels and typically need heavier coils to produce the extra power needed to drive the ink into the skin, while liners typically have thinner barrels and lighter coils for extra comfort.

A conventional rotary tattoo machine uses an electric motor with a rotatable shaft that is coupled with the needle to drive the needle in the reciprocating up and down motion. Rotary tattoo machines can offer several advantages to the coil machines in that a rotary tattoo machine is typically lighter weight, substantially less noisy, and can be used as either a liner or a shader. However, the rotary tattoo machines typically do not allow the needle to "give" (i.e., absorb some of the impact force between the needle and the skin) when the machine is pushed too hard against the skin, which can result in blowout when the needle pierces too far into or beyond the dermal layer of skin.

In view of the shortcomings in conventional tattoo machines, it would be advantageous to provide a tattoo machine which is relatively quieter, lighter and more versatile as well as capable of providing "give" in the needle to reduce or even eliminate blowout.

BRIEF SUMMARY

Various embodiments of the present disclosure comprise tattoo machines configured to provide "give" in the needle for reducing or even eliminating blowout, while also providing quieter operation, lighter weight and increased versatility. In one or more embodiments, a tattoo machine may comprise a frame, and a motor pivotably coupled to the frame. The motor may include an eccentrically weighted shaft. A needle drive mechanism may be coupled with the motor in order to facilitate driving a needle when the motor is energized.

Other embodiments of the disclosure comprise methods of making a tattoo machine. One or more implementations of such methods may comprise obtaining a frame, obtaining a motor that includes an eccentrically weighted shaft, and coupling the motor to the frame so that the motor is able to pivot about a pivot axis.

Still additional embodiments of the disclosure comprise methods operational of a tattoo machine. According to one or more implementations of such methods, an eccentrically weighted shaft is rotated on a motor that is pivotably coupled to a frame. In response to the rotation of the eccentrically weighted shaft, the motor is pivoted about a pivot axis.

DETAILED DESCRIPTION

The illustrations presented herein are, in some instances, not actual views of any particular housing assembly, motor assembly, or tattoo machine, but are merely idealized representations which are employed to describe various features associated with one or more embodiments of the present disclosure. Additionally, elements common between figures may retain the same numerical designation.

Figure 1:
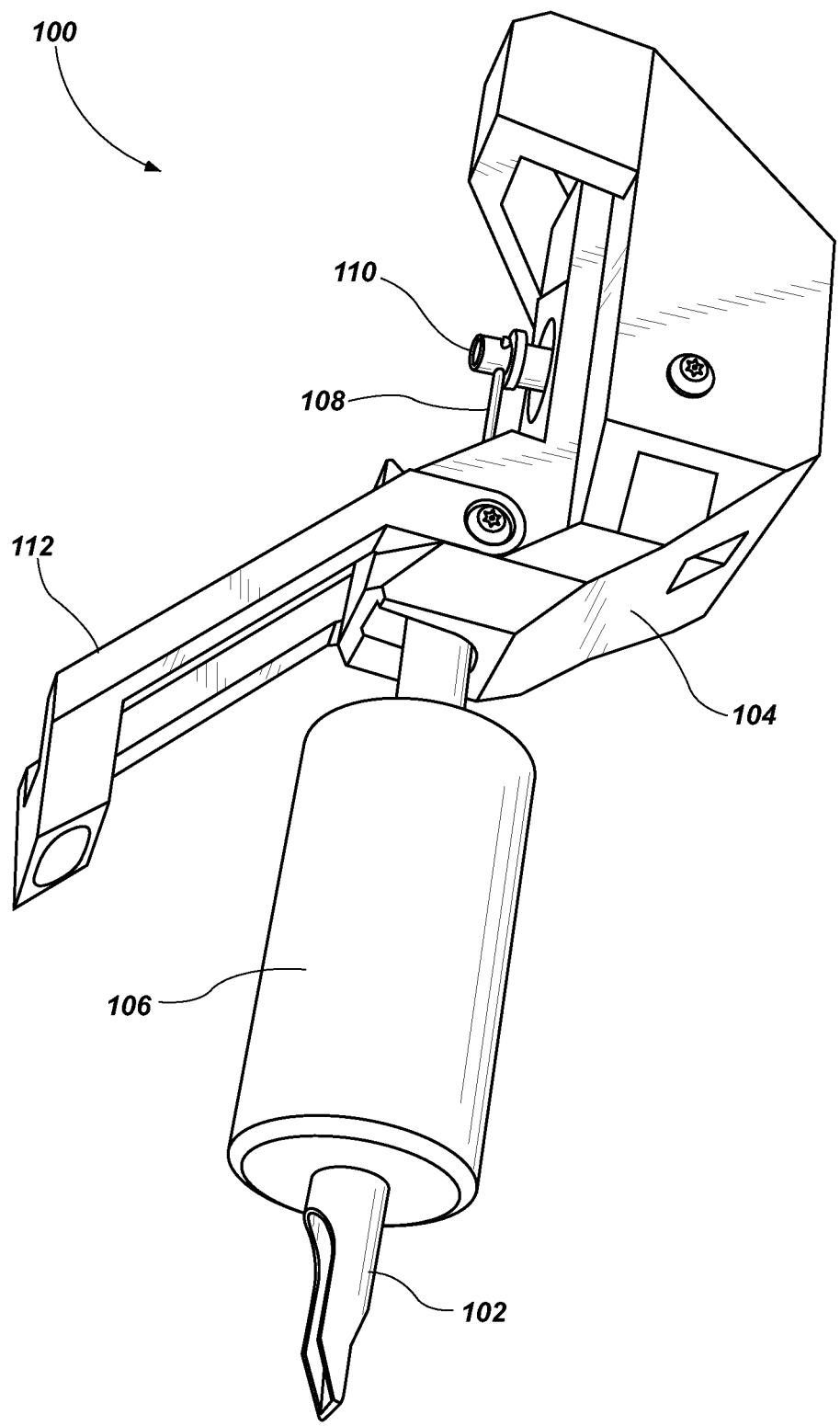
FIG. 1 is an isometric view of a tattoo machine according to at least one example of an embodiment of the present disclosure.

Various embodiments of the present disclosure are directed toward tattoo machines. Referring to FIG. 1, an isometric view of a tattoo machine 100 is shown according to at least one embodiment. Generally, the tattoo machine 100 comprises a tube 102 that is coupled to a frame 104. The tube 102 can include a grip 106 coupled thereto or integral therewith.

Such a tube 102 and grip 106 configuration can be similar to the tubes and grips employed in conventional tattoo machines. The tube 102 and grip 106 may be made from the same or different materials. By way of example and not limitation, the tube 102 and/or grip 106 may be formed from a metal or metal alloy, a polymer, a ceramic, or any other suitable material, as well as combinations thereof.

As shown in the illustrated embodiment, the frame 104 can be formed as a housing in some embodiments. In other embodiments, the frame 104 can be formed with a more simple configuration comprising features adapted to be coupled with various components as described herein, without necessarily housing the components. The frame 104 may comprise any suitable material, including but not limited to a metal or metal alloy, a polymer, a ceramic material, or other suitable material, as well as combinations thereof.

The tattoo machine 100 may also include a needle 108 positioned to extend through the inside of the tube 102 and is coupled to a needle drive mechanism 110, such as a needle arm. The needle 108 can comprise any of the various kinds of conventional tattoo needles known generally to those of ordinary skill in the art.

In some environments and/or according to the preference of a user, it may be desirable to provide additional lighting to the surface of the skin surface being tattooed. Accordingly, the frame 104 can be configured to receive an optional lighting mechanism 112 that may be fixedly or removably coupled thereto to provide additional light to the skin surface being tattooed.

Figure 2:
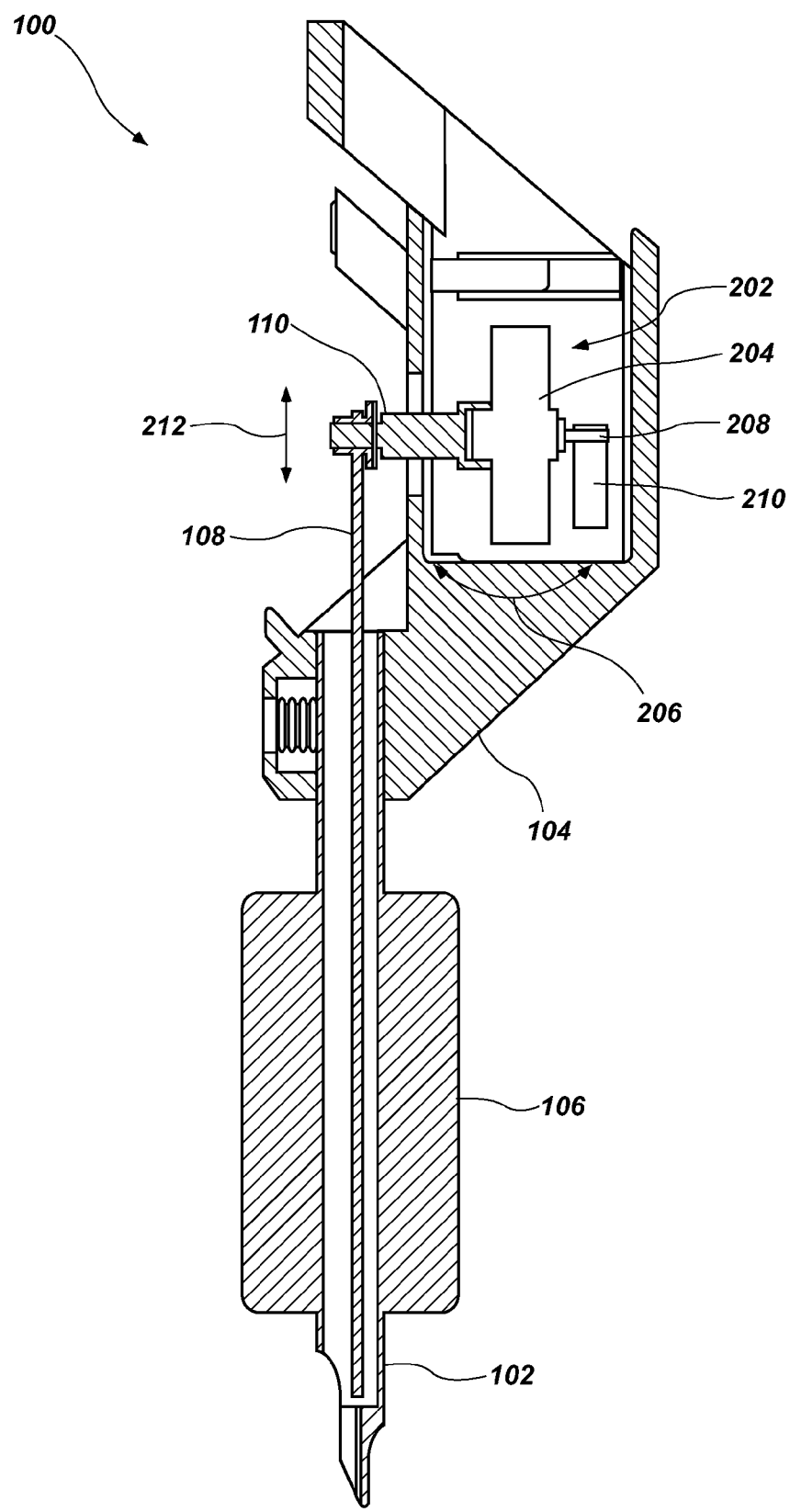
FIG. 2 is a cross-sectional view of the tattoo machine of FIG. 1 according to at least one embodiment.

The needle drive mechanism 110 that is coupled with the needle 108 comprises a portion of a motor assembly. Turning to FIG. 2, a cross-sectional view of the tattoo machine 100 is illustrated showing at least some components of a motor assembly 202 within the frame 104. As illustrated, a needle drive mechanism 110 configured as a needle arm is coupled to a motor 204 positioned in the frame 104. The motor 204 is pivotably positioned within the frame 104 to enable the motor 204 to move in the direction of arrows 206 when energized. The motor 204 can comprise a conventional electric motor, such as a conventional DC electric motor, and includes a rotatable shaft 208 extending from a portion thereof.

According to a feature, the shaft 208 of the motor 204 is configured to be eccentrically weighted. For example, the shaft 208 itself may be formed in such a manner as to have an integral eccentric weight portion, or an eccentric weight 210 may be coupled to the shaft 208, as well as some combination thereof. As the shaft 208 is rotated, the eccentric weight 210 causes the motor 204 to pivot in the direction of arrows 206, causing the needle drive mechanism 110 to displace an attached needle 108 up and down, as indicated by arrows 212.

Figure 3:
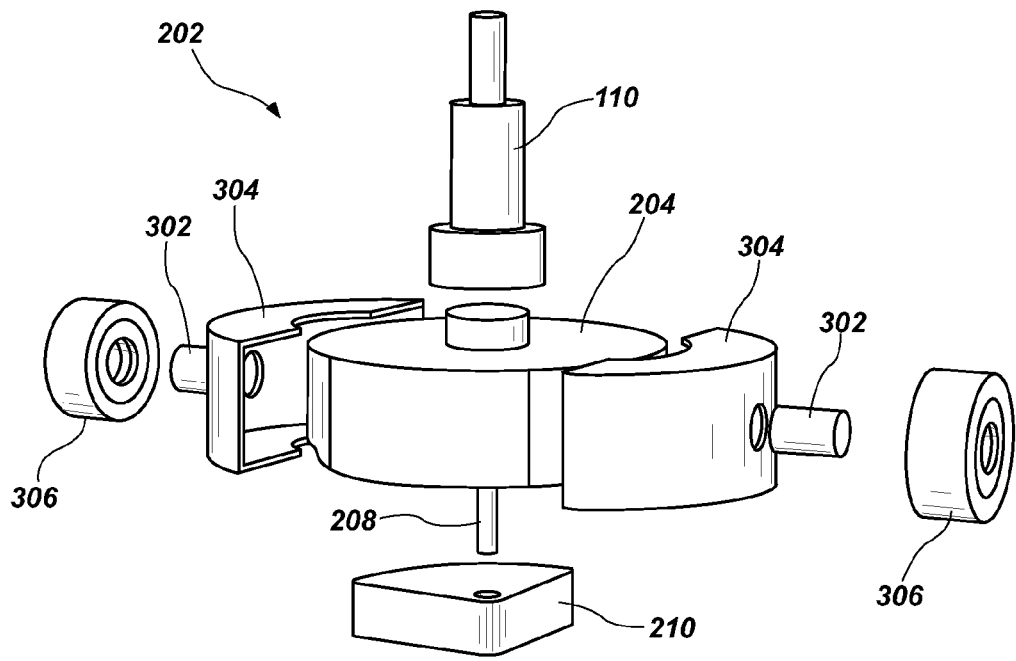
FIG. 3 shows an isometric exploded view of a motor assembly according to at least one embodiment.
Figure 4:
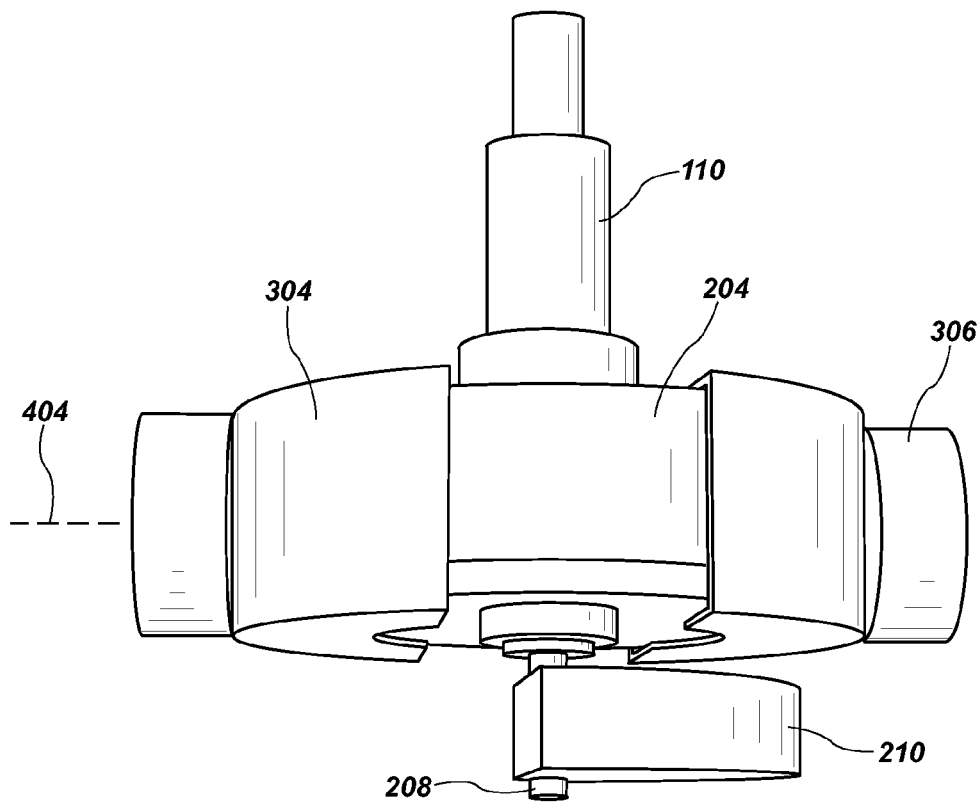
FIG. 4 illustrates an isometric view of the motor assembly 202 when put together.

FIG. 3 shows an isometric exploded view of the motor assembly 202 according to at least one embodiment, and FIG. 4 illustrates an isometric view of the motor assembly 202 when assembled. As shown, the motor assembly 202 may comprise the motor 204 coupled with the needle drive mechanism 110 and the shaft 208. Pivot axels 302 can be coupled with the motor 204 to enable the motor 204 to rotate about the pivot axels 302 during operation. In at least some embodiments, the pivot axels 302 are coupled to the motor 204 by means of a sleeve 304. For instance, the sleeve 304 can be coupled to the motor 204, and the pivot axels 302 can be coupled to the sleeve 304 or the pivot axels 302 may be integral to the sleeve 304. The sleeve 304 can be adapted to encompass at least a portion of the motor 204, with two sides coupled together around the motor 204 and/or with the portions of the sleeve 304 coupled directly to the motor 204. In one or more other embodiments, the pivot axels 302 can coupled to the motor by being attached directly to the motor 204 and/or formed integral to the motor 204.

The pivot axels 302 can be coupled with bearings 306 to facilitate a smooth pivoting motion of the motor 204 during operation. In other embodiments, the pivot axels 302 may be coupled directly to the frame (e.g., frame 104 in FIGS. 1 and 2). For example, a portion of each of the pivot axels 302 extending away from the motor 204 may be disposed in an aperture in the frame. The pivot axels 302 are depicted as being fixedly attached to the motor 204 so that the pivot axels 302 rotate with the motor 204. In other embodiments, however, the pivot axels 302 may be positioned to extend into an aperture associated with the motor 204 such that the motor 204 rotates on the pivot axels 302 while the pivot axels 302 remain at least substantially fixed.

The needle drive mechanism 110 generally comprises a component adapted to enable a needle to be driven when a motor 204 is energized. In some embodiments, the needle drive mechanism 110 may comprise a needle arm or other shaft configuration to extend from the motor 204 and facilitate coupling a needle 108 with the motor 204. In other embodiments, the needle drive mechanism 110 may simply comprise a feature adapted to facilitate coupling the needle to the body of the motor 204 and/or the sleeve 304.

The needle drive mechanism 110 may be coupled with the body of the motor 204 and/or the sleeve 304 in some examples. In other examples, the body of the motor 204 and/or the sleeve 304 may be formed with an integral needle drive mechanism 110. In embodiments where the needle drive mechanism 110 comprises a needle arm or other shaft, the needle drive mechanism 110 can be positioned to a side of the motor 204 directly opposite from the motor shaft 208 and extending away from the motor 204 in a direction opposite from the motor shaft 208, as illustrated. It should be apparent to a person of ordinary skill in the art, however, that the needle drive mechanism 110 embodied as a needle arm or other shaft can be positioned on other surfaces and/or portions of the motor 204, so long as the needle drive mechanism 110 facilitates driving the up and down motion of a needle during use. The needle drive mechanism 110 can be disposed so that the needle drive mechanism 110 extends from the motor 204 in a direction at least substantially transverse to a pivot axis of the motor 204 (e.g., pivot axis 404 in FIG. 4) in some implementations. In other implementations, the needle drive mechanism may extend in a direction at least substantially parallel to the pivot axis of the motor 204 (e.g., pivot axis 404 in FIG. 4), but offset from the pivot axis of the motor 204 so that the needle drive mechanism is displaced when the motor 204 is pivoted about the pivot axis.

As shown in FIG. 4, when the motor 204 is energized, the shaft 208 rotates, as indicated by the arrow 402. The motor 204 can be energized by providing an electrical current thereto in a conventional manner, resulting in rotation of the shaft 208. As the shaft 208 is rotated, the motor 204 pivots about the pivot axis 404. Because the shaft 208 is eccentrically weighted and/or has an eccentric weight 210 coupled thereto, a centripetal force is generated toward the shaft 208 and an equal, but opposite reactive centrifugal force results toward the center of mass of the eccentric weight 210.

In conventional systems, a motor is mounted in a manner to inhibit movement of the motor as a result of any such forces. However, in various embodiments of the present tattoo machine, the motor 204 is pivotably mounted so that the motor 204 can move about the pivot axis 404, while inhibiting motion of the motor 204 in other directions as a result of the forces generated by the rotating eccentric weight 210. That is, with the motor 204 coupled to the frame (e.g., frame 104 in FIGS. 1 & 2) with pivot axels 302 axially aligned with the pivot axis, the motor 204 is able to pivot in a direction about the pivot axis 404. Therefore, when the motor 204 is energized and the shaft 208 is rotating, the motor 204 will pivot about the axis 404 as a result of the centripetal force. This rotation about the axis 404 results in displacement of the needle drive mechanism 110 as shown by arrow 212 in FIG. 2, which displacement of the needle drive mechanism 110 drives the displacement of an attached needle.

Figure 5:
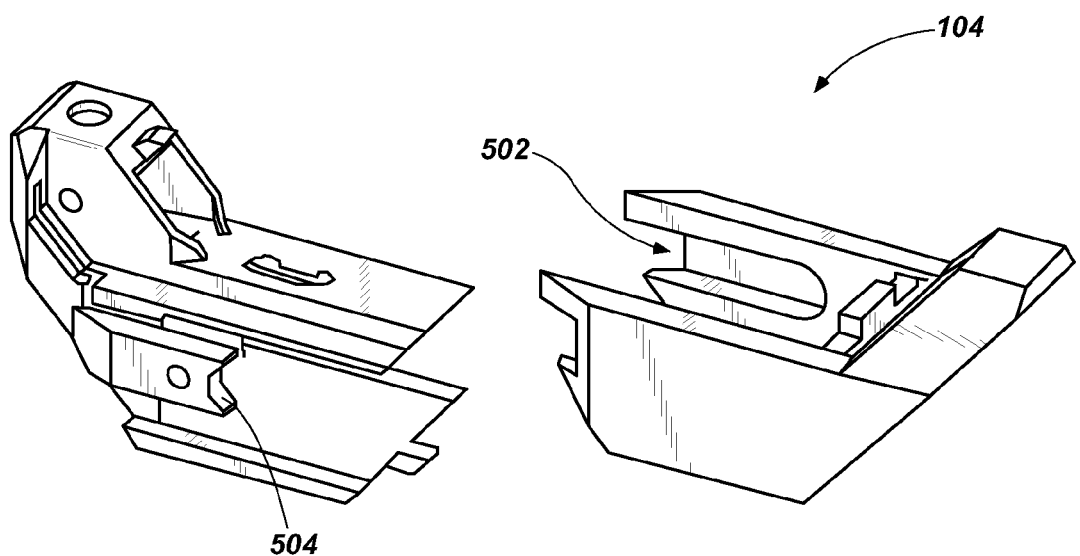
FIG. 5 is an isometric exploded view of at least one embodiment of a frame.

FIG. 5 shows an isometric view of a frame 104 according to at least one embodiment. As shown, the frame 104 can comprise two or more pieces assembled together, and may include a motor attachment feature for pivotably coupling the motor 204 to the frame 104. In the embodiment shown, one section of the frame 104 includes a slot 502 sized and configured for receiving the bearings 306 of the motor assembly, with the other section including a protruding feature 504 adapted to slide into the slot 502 and retain the bearings 306 in the slot 502 when the frame 104 is assembled.

Figure 6:
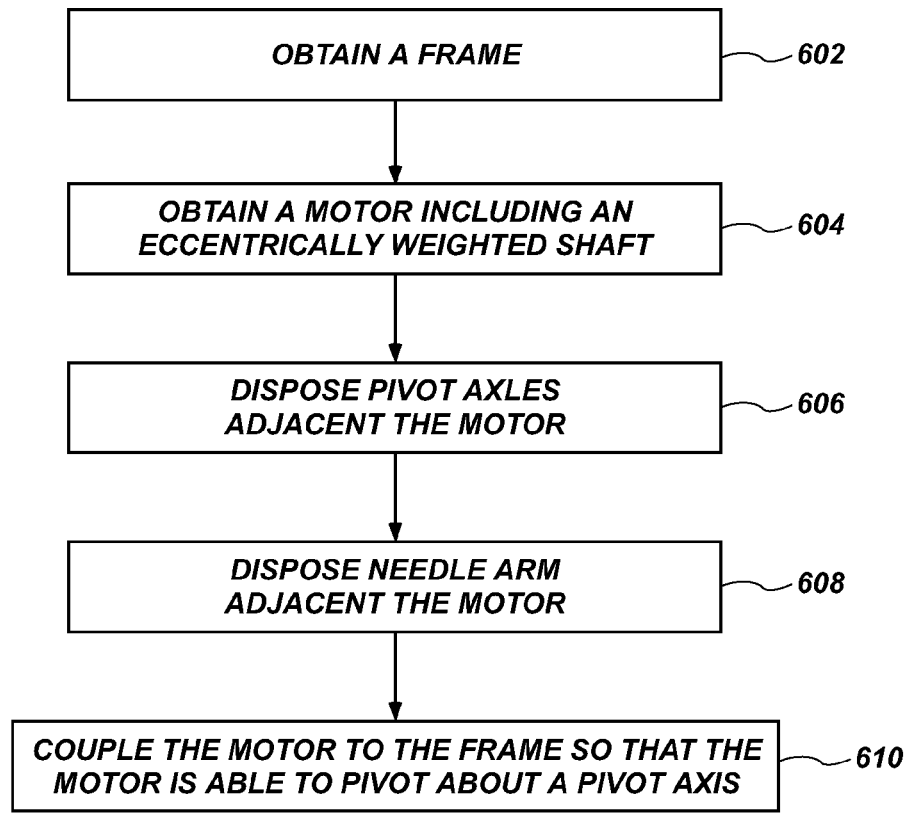
FIG. 6 is a flow diagram illustrating an example of a method of making a tattoo machine according to at least one implementation.

Further embodiments of the present disclosure relate to methods of making tattoo machines. FIG. 6 is a flow diagram illustrating an example of a method 600 for making a tattoo machine according to at least one implementation. With reference to FIGS. 2 and 6, a frame 104 can be obtained at step 602. For example, a frame 104 can be formed in any conventional manner, such as by machining, casting, molding, and/or otherwise forming one or more components of the frame 104. If components of the frame 104 are formed or otherwise obtained separately, the components can then be coupled together. In at least some implementations, the frame 104 may include the slots 502 and protruding feature 504 described above with reference to FIG. 5.

At step 604, a motor 204 may be obtained, where the motor 204 includes an eccentrically weighted shaft 208. According to various implementations, the shaft 208 can be formed to include an integral eccentric weight portion (e.g., the shaft 208 can be formed eccentrically weighted), an eccentric weight 210 can be coupled to the shaft 208, or the shaft 208 may include both an integral eccentric weight portion and an eccentric weight 210 coupled thereto.

At step 606, pivot axels 302 (shown in FIG. 3) may be disposed adjacent the motor 204, where the pivot axels 302 are axially aligned with the pivot axis 404 (shown in FIG. 4). In some implementations, the pivot axels 302 are coupled to the motor 204. For example, the pivot axels 302 may be coupled to the motor 204 by means of a sleeve 304. In other examples, the pivot axels 302 can be coupled directly to the motor 204 using, for instance, an adhesive or weld. In other implementations, the pivot axels 302 may be disposed adjacent the motor 204 by the pivot axels 302 being integrally formed with the motor 204.

At step 608, a needle drive mechanism 110 is disposed adjacent the motor 204. The needle drive mechanism 110 can be disposed as to extend away from the motor 204 in a direction transverse to the pivot axis 404 (shown in FIG. 4). The needle drive mechanism 110, in some examples, is disposed adjacent a portion of the motor opposite from the eccentrically weighted shaft 208. In some implementations, the needle drive mechanism 110 may be attached to the motor 204 using, for example, an adhesive and/or a weld. In other implementations, the needle drive mechanism 110 can be formed integral with the motor 204.

At step 610, the motor 204 can be coupled to the frame 104 in such a manner as to enable the motor 204 to pivot about the pivot axis 404 (shown in FIG. 4). For example, the pivot axels 302 (shown in FIG. 3) disposed adjacent the motor 204 can be coupled to the frame 104 so that the motor 204 can pivot about the pivot axels 302. In some implementations, the pivot axels 302 can be coupled to the frame 104 either directly or through one or more other components, such as the bearings 306 (shown in FIG. 3).

According to other steps, a tube 102 can be coupled to the frame 104 and a needle 108 may be disposed through the tube 102 and coupled to the needle drive mechanism 110. In the preceding detailed description, embodiments have been described in terms of a process that may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged.

One or more of the various features described and depicted herein provide tattoo machines that allow some "give" in the needle (i.e., absorb some of the force resulting when the needle impacts the skin), inhibiting blowout that is caused when the needle extends too far into or beyond the dermal layer of skin, while also providing relatively light weight, relatively low noise, and the ability for use as either a liner or a shader.

While certain embodiments have been described and shown in the accompanying drawings, such embodiments are merely illustrative and not restrictive of the scope of the disclosure, and this disclosure is not limited to the specific constructions and arrangements shown and described, since various other additions and modifications to, and deletions from, the described embodiments will be apparent to one of ordinary skill in the art. Thus, the scope of the disclosure is only limited by the literal language, and equivalents, of the claims which follow.

What is claimed is:

1. A tattoo machine, comprising:
    a frame;
    a motor pivotably coupled to the frame, the motor including an eccentrically weighted shaft; and
    a needle drive mechanism coupled with the motor.

2. The tattoo machine of claim 1, wherein the eccentrically weighted shaft comprises an eccentric weight portion integral to the shaft.

3. The tattoo machine of claim 1, wherein the eccentrically weighted shaft comprises an eccentric weight coupled to the shaft.

4. The tattoo machine of claim 1, wherein the eccentrically weighted shaft comprises an eccentric weight portion integral to the shaft and eccentric weight coupled to the shaft.

5. The tattoo machine of claim 1, wherein the needle drive mechanism is coupled to the motor to extend away from the motor in a direction opposite from the eccentrically weighted shaft.

6. The tattoo machine of claim 1, further comprising pivot axels coupled with the motor and axially aligned with the pivot axis.

7. The tattoo machine of claim 6, further comprising a sleeve coupled to the motor, wherein the pivot axels are coupled to the motor by means of the sleeve.

8. The tattoo machine of claim 1, further comprising a tube coupled to the frame.

9. A method of making a tattoo machine, comprising:
    obtaining a frame;
    obtaining a motor comprising an eccentrically weighted shaft; and
    coupling the motor to the frame so that the motor is able to pivot about a pivot axis.

10. The method of claim 9, wherein obtaining a motor comprising an eccentrically weighted shaft comprises:

obtaining the motor with the shaft comprising an eccentric weight coupled to the shaft, an eccentric weight portion formed integral to the shaft, or both an eccentric weight portion integral to the shaft and an eccentric weight coupled to the shaft.

11. The method of claim 9, further comprising:

disposing pivot axels adjacent the motor, wherein the pivot axels are axially aligned with the pivot axis.

12. The method of claim 11, wherein disposing the pivot axels adjacent the motor comprises:

coupling a sleeve to the motor, wherein the sleeve includes the pivot axels disposed therewith.

13. The method of claim 11, wherein coupling the motor to the frame comprises:

coupling the pivot axels with the frame so that the motor is able to pivot about the pivot axels in relation to the frame.

14. The method of claim 9, further comprising:

coupling a needle drive mechanism with the motor, where the needle drive mechanism is adapted to facilitate driving a needle when the motor is energized.

15. The method of claim 14, wherein coupling the needle drive mechanism with the motor comprises positioning the needle drive mechanism on the motor opposite from the eccentrically weighted shaft.

16. A method operational of a tattoo machine, comprising:

rotating an eccentrically weighted shaft on a motor pivotably coupled to a frame; and pivoting the motor about a pivot axis as a result of the rotation of the shaft.

17. The method of claim 16, wherein rotating the eccentrically weighted shaft on the motor comprises:

rotating a shaft comprising an integral eccentric weight portion, an eccentric weight coupled to the shaft, or both an integral eccentric weight portion and an eccentric weight coupled to the shaft.

18. The method of claim 16, wherein rotating the eccentrically weighted shaft on the motor comprises:

generating a centripetal force is in a direction toward the shaft.

19. The method of claim 16, further comprising:

displacing a needle drive mechanism in response to pivoting the motor.

20. The method of claim 19, further comprising:

linearly displacing a tattoo needle coupled to the needle drive mechanism.

* * * * *